United States Patent
Fong et al.

(10) Patent No.: US 8,404,493 B2
(45) Date of Patent: Mar. 26, 2013

(54) MULTIPLE ANALYTE IMMUNOASSAY

(75) Inventors: Whalley K. Fong, Coquitlam (CA); Paul C. Harris, Bothell, WA (US); Brian G. Richards, N. Vancouver (CA)

(73) Assignee: Response Biomedical Corporation, Vancouver (CA)

( * ) Notice: Subject to any disclaimer, the term of this patent is extended or adjusted under 35 U.S.C. 154(b) by 752 days.

(21) Appl. No.: 12/478,305

(22) Filed: Jun. 4, 2009

(65) Prior Publication Data

US 2010/0047857 A1    Feb. 25, 2010

Related U.S. Application Data

(63) Continuation of application No. PCT/US2007/025268, filed on Dec. 11, 2007.

(60) Provisional application No. 60/874,315, filed on Dec. 12, 2006.

(51) Int. Cl.
*G01N 33/558* (2006.01)

(52) U.S. Cl. ........ 436/514; 422/400; 422/401; 422/420; 422/425; 435/287.7; 435/287.9; 435/805; 435/810; 435/970; 435/973; 436/810

(58) Field of Classification Search .................. None
See application file for complete search history.

(56) References Cited

U.S. PATENT DOCUMENTS

| | | | |
|---|---|---|---|
| 6,509,196 B1 * | 1/2003 | Brooks et al. | 436/514 |
| 7,175,992 B2 * | 2/2007 | Fong | 435/7.9 |
| 7,691,595 B2 * | 4/2010 | Fong | 435/7.9 |
| 2003/0199004 A1 * | 10/2003 | Fong | 435/7.9 |
| 2006/0240541 A1 | 10/2006 | Petruno et al. | |
| 2007/0065952 A1 * | 3/2007 | Harris et al. | 436/514 |

FOREIGN PATENT DOCUMENTS

| | | |
|---|---|---|
| EP | 1 361 435 A1 | 11/2003 |
| EP | 1 500 872 A2 | 7/2005 |
| WO | WO 01/50129 A2 | 7/2001 |
| WO | WO 2006/083367 A2 | 8/2006 |
| WO | WO 2007/024633 A2 | 3/2007 |
| WO | WO 2008/073393 A1 | 6/2008 |

OTHER PUBLICATIONS

International Search Report for PCT Application No. WO 2008/073393, mailed Apr. 23, 2008.
International Preliminary Report on Patentability and Written Opinion of the International Searching Authority for International Application No. PCT/US2007/025268 mailed on Jun. 25, 2009.

* cited by examiner

*Primary Examiner* — Chris L Chin
(74) *Attorney, Agent, or Firm* — Jun He Law Offices P.C.; James J. Zhu

(57) ABSTRACT

Methods for measuring the amount of two or more analytes of interest in a fluid sample, and kits useful in the methods, are disclosed. The methods involve determining a ratio of a detected amount of a single analyte of interest, to the sum of a detected amount of each of the analytes of interest plus a detected amount of a control, wherein the amount of each analyte of interest is directly or inversely related to the ratio for each analyte of interest.

6 Claims, No Drawings

MULTIPLE ANALYTE IMMUNOASSAY

RELATED APPLICATIONS

This application is a continuation of International Application No. PCT/US2007/025268, which designated the United States and was filed on Dec. 11, 2007, published in English, which claims the benefit of U.S. Provisional Application No. 60/874,315, filed on Dec. 12, 2006. The entire teachings of the above applications are incorporated herein by reference.

BACKGROUND OF THE INVENTION

Quantitative analysis of cells and analytes in fluid samples, particularly bodily fluid samples, often provides critical diagnostic and treatment information for physicians and patients. Quantitative immunoassays utilize the specificity of the antigen (Ag)-antibody (Ab) reaction to detect and quantitate the amount of an Ag or Ab in a sample. In solid phase immunoassays, one reagent (e.g., the Ag or Ab) is attached to a solid surface, facilitating separation of bound reagents or analytes from free reagents or analytes. The solid phase is exposed to a sample containing the analyte, which binds to its Ag or Ab; the extent of this binding is quantitated to provide a measure of the analyte concentration in the sample. Transduction of the binding event into a measurable signal, however, is affected by a number of limitations, including constraints of particle movement on the solid phase, which affect the specificity and applicability of quantitative immunoassays. In addition, related analytes of interest may compete with one another in an assay, rendering it difficult to assess correctly the presence of more than one analyte of interest.

SUMMARY OF THE INVENTION

The invention relates to methods of measuring the amount of two or more analytes of interest in a fluid sample, using a solid phase assay (e.g., a sandwich immunoassay or an inhibition immunoassay), in which an analyte of interest and a capture reagent are used as part of a specific binding pair; and to kits for use in the methods. In the methods of the invention, a ratio of a detected amount of a single analyte of interest, to the sum of a detected amount of each of the analytes of interest plus a detected amount of a control, is determined, wherein the amount of each analyte of interest is directly or inversely related to the ratio for each analyte of interest. In certain embodiments, a detected background amount is subtracted from the detected amount of each analyte of interest and from the control prior to determining the ratios.

The methods of the invention utilize a solid phase apparatus, such as a lateral flow solid phase apparatus or a capillary flow apparatus. In representative methods of the invention, the solid phase apparatus includes an application point, two or more sample capture zones (one corresponding to each analyte of interest) and a control capture zone; the sample capture zones and the control capture zone can be sequentially (with respect to the flow of liquid by capillary action) located on the solid phase apparatus; alternatively, the sample capture zones and the control capture zone can be approximately equidistant from the application point. A sample capture reagent (e.g., an agent that binds to the analyte of interest, such as an antibody to the analyte of interest) is adsorbed in each of the sample capture zones, one for each analyte of interest. A control capture reagent (e.g., an agent that binds to the analyte binding particles, such as an anti-immunoglobulin antibody) is adsorbed in the control capture zone.

Also provided is a sample collection apparatus containing a population of particles, such as liposomes, colloidal gold, or organic polymer latex particles, stored in a stable form. In sandwich immunoassays of the invention, the particles are analyte binding particles that are coated with a binding agent (e.g., an antibody) to the analyte of interest, or are coated with a binding agent to multiple analytes of interest; alternatively, different populations of analyte binding particles, each coated with a binding agent to one of the analytes of interest, are utilized. In competitive or inhibition assays, the particles are "analyte coated" particles that are coated with analyte of interest, or are coated with multiple analytes of interest; alternatively, different populations of analyte coated particles, each coated with one of the analytes of interest, are utilized. In either type of assay, the particles can be labeled, using a calorimetric, fluorescent, luminescent, chemiluminescent, or other appropriate label, to facilitate detection.

In one embodiment of the methods, a fluid sample to be assessed for two or more analytes of interest is introduced into the sample collection apparatus, and a buffer is subsequently introduced into the mixed fluid sample. In another embodiment of the methods, a buffer is introduced into the sample collection apparatus, and the fluid sample to be assessed for the analytes of interest is subsequently introduced. In a third embodiment of the methods, the fluid sample is formed by introducing a solid into a buffer, and the fluid sample is subsequently introduced into the sample collection apparatus. In any of these embodiments, a buffered, mixed fluid sample containing the particles is produced.

In the sandwich assay, analytes of interest present in the sample interact with the analyte binding particles, resulting in contacted analyte binding particles within the mixed fluid sample. The buffered, mixed fluid sample is applied to the application point of the solid phase apparatus. The solid phase apparatus is then maintained under conditions which are sufficient to allow capillary action of fluid to transport particles to and through the sample capture zones and to and through the control capture zone. The sample capture reagent interacts with contacted analyte binding particles, resulting in arrest of particles in the sample capture zones. Capillary action of the fluid also mobilizes the contacted analyte binding particles not only to and through the sample capture zones, but also to and through the control capture zone, where they bind to the control capture reagent. The amount of analyte binding particles that are arrested in each sample capture zone, and in the control capture zone, are then determined.

The amount of an analyte of interest in the fluid sample is then determined. For example, the amount of an analyte of interest in the fluid sample can be determined as a ratio between 1) the amount of analyte binding particles that are arrested in the sample capture zone corresponding to that analyte of interest, and 2) the sum of the amount of analyte binding particles in all of the sample capture zones and in the control capture zone. In another embodiment, if desired, a detected background amount is subtracted from the detected amount of particles in each of the sample capture zones and in the control capture zone prior to determining the ratios.

In a competitive or inhibition type of assay, the buffered, mixed fluid sample is applied to the application point of the solid phase apparatus. The solid phase apparatus is then maintained under conditions which are sufficient to allow capillary action of fluid to transport analyte coated particles to and through the sample capture zones, and to and through the control capture zone, where they bind to the control capture reagent. The sample capture reagents interact with analyte coated particles; interaction of sample capture reagents and analyte coated particles results in arrest of analyte coated particles in the sample capture zones. Because of competition between the analyte coated particles and analyte (if present) in the sample for binding sites on the sample capture reagents in the sample capture zones, the amount of analyte coated particles arrested in the sample capture zones is inversely proportional to the amount of the analytes in the sample. The amount of analyte coated particles that are arrested in the sample capture zones, and in the control capture zone, are then determined.

The amount of an analyte of interest in the fluid sample is then determined. For example, the amount of an analyte of interest in the fluid sample is inversely related to a ratio between 1) the amount of analyte coated particles that are arrested in the sample capture zone corresponding to that analyte of interest, and 2) the sum of the amount of analyte coated particles in all of the sample capture zones and in the control capture zone. In another embodiment, if desired, a detected background amount is subtracted from the detected amount of particles in each of the sample capture zones and in the control capture zone prior to determining the ratios.

DETAILED DESCRIPTION OF THE INVENTION

A description of example embodiments of the invention follows. The teachings of all patents, published applications and references cited herein are incorporated by reference in their entirety.

The present invention pertains to methods of quantitatively measuring the amount of two or more analytes of interest using solid phase assays, and kits therefor. The solid phase assays of the invention are lateral flow solid phase assays or capillary flow solid phase assays.

An assay, as used herein, refers to an in vitro procedure for analysis of a sample to determine the presence, absence, or quantity of analytes. The assays of the inventions utilize at least two analytes of interest and analyte binding agents that correspond to the analytes of interest. Each analyte of interest and its analyte binding agent are members of a specific binding pair, in which a first member of the binding pair (e.g., analyte) reacts specifically with a second member (e.g., the binding agent). One or both members of the binding pair can be an antibody. For example, a first member of the binding pair (e.g., an analyte of interest) can be an antibody, and a second member of the binding pair (e.g., a binding agent) can be anti-immunoglobulin antibody; alternatively, the first member of the binding pair (e.g., the analyte) can be an antigen, and the second member of the binding pair (e.g., the binding agent) can be an antibody.

In one embodiment, the assay is an immunoassay which utilizes antibodies as a component of the procedure. In a preferred embodiment, the immunoassay is a sandwich assay, which is a test for analyte in which a fluid sample to be assessed for the presence or absence, or quantity of analyte, is contacted with particles coated with an analyte binding agent, such as antibodies to the analyte, and the resultant mixture is applied to a solid phase and subsequently moves by capillary action through the solid phase. A positive result is indicated by detection of interaction between analyte and analyte binding agent-coated particles in a capture zone of the solid phase, the amount of analyte binding agent-coated particles in the capture zone being related to the amount of analyte in the fluid sample. In another preferred embodiment, the immunoassay is an inhibition or competitive assay, which is a test for analyte in which a fluid test sample to be assessed for the presence or absence, or quantity of analyte, is contacted with particles coated with the analyte, and the resultant mixture is applied to a solid phase and subsequently moves by capillary action through the solid phase. A positive result is indicated by detection of interaction between analyte binding agent and analyte coated particles in a capture zone of the solid phase, the amount of analyte coated particles in the capture zone being inversely related to the amount of analyte in the fluid sample.

In other embodiments of the assays of the invention, neither an analyte nor its binding agent in a specific binding pair are antibodies: for example, the first member of the binding pair can be a ligand, and the second member of the binding pair can be a receptor; alternatively, the first member of the binding pair can be a lectin, and the second member of the binding pair can be a sugar. In still another embodiment, the first member of the binding pair can be a nucleic acid (e.g., DNA, RNA), and the second member of the binding pair can be a nucleic acid which specifically hybridizes to the first member of the binding pair. Specific hybridization, as used herein, refers to the ability of a first nucleic acid to hybridize to a second nucleic acid in a manner such that the first nucleic acid does not hybridize to any nucleic acid other than to the second nucleic acid (e.g., when the first nucleic acid has a higher similarity to the second nucleic acid than to any other nucleic acid in a sample wherein the hybridization is to be performed). "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity which is less than perfect (e.g., 70%, 75%, 80%, 85%, 90%, 95%). For example, certain high stringency conditions can be used which distinguish perfectly complementary nucleic acids from those of less complementarity. "High stringency conditions", "moderate stringency conditions" and "low stringency conditions" for nucleic acid hybridizations are explained on pages 2.10.1-2.10.16 and pages 6.3.1-6.3.6 in *Current Protocols in Molecular Biology* (Ausubel, F. M. et al., *Current Protocols in Molecular Biology*, John Wiley & Sons, (1998), the entire teachings of which are incorporated by reference herein). The exact conditions which determine the stringency of hybridization depend not only on ionic strength (e.g., 0.2× SSC, 0.1×SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, equivalent conditions can be determined by varying one or more of these parameters while maintaining a similar degree of identity or similarity between the two nucleic acid molecules.

Regardless of the composition of an analyte and its binding agent, these two components nevertheless form a specific binding pair, in which the first member reacts specifically with the second member. Specific interaction between the members of the binding pair indicates that the first member of the binding pair preferentially binds or otherwise interacts with the second member of the binding pair, preferably to the exclusion of any binding to another compound in the assay.

The terms, analyte or analyte of interest, as used herein, refer to a first member of a binding pair as described above. The analyte is a molecule or compound for which the amount will be measured. The analyte can be in the form of a solid, such as a dry substance (e.g., a powder, a particulate; spore; or other particle), or can be in the form of a fluid (e.g., a solid as described above that has been dissolved or suspended in a fluid; or other liquid sample). Examples of analytes include bacteria; spores; proteins, such as hormones or enzymes; glycoproteins; peptides; small molecules; polysaccharides; antibodies; nucleic acids; drugs; toxins (e.g., environmental toxins); viruses or virus particles; portions of a cell wall; and other compounds. In a preferred embodiment, each analyte is "immunogenic," which indicates that antibodies (as described below) can be raised to that analyte, or to analyte that is bound to a carrier (e.g., a hapten-carrier conjugate, for which antibodies can be raised to the hapten). In some representative embodiments, a first analyte of interest can be influenza type A, and a second analyte of interest can be influenza type B. The analytes of interest can be in a liquid sample; alternatively, the analytes of interest can be in a dry (non-fluid) sample (e.g., a solid, such as a particulate sample, powder sample, or soil sample). Each analyte of interest is a first member of a binding pair as described above—i.e., each analyte of interest reacts specifically with a second member of a binding pair.

In the methods of the invention, a fluid sample is assessed for the presence or absence, or quantity, of two or more analytes of interest. The fluid can be a fluid that wets the material of the solid phase; that supports a reaction between each analyte of interest and its analyte binding agent, such as the antibody/antigen reaction (i.e., does not interfere with antibody/antigen interaction); and that has a viscosity that is sufficiently low to allow movement of the fluid by capillary action. In a preferred embodiment, the fluid is an aqueous solution (such as a bodily fluid). The fluid sample can be a fluid having relatively few components, for example, an aqueous solution containing the analyte of interest; alternatively, the fluid sample can be a fluid having many components, such as a complex environmental sample (e.g., sewage, waste water, groundwater, or other water sample), or a complex biological fluid (e.g., whole blood, plasma, serum, urine, cerebrospinal fluid, saliva, semen, vitreous fluid, synovial fluid, or other biological fluid). In a preferred embodiment in which the fluid is a biological fluid, the fluid is whole blood, plasma, or serum. In another preferred embodiment in which the fluid is a biological fluid, the fluid is a mucosal fluid. If desired, the fluid sample can be diluted; for example, if a complex biological fluid is used as the fluid sample, it can be diluted with a solution (e.g., an aqueous solution).

If one of the analytes of interest is not in solution (e.g., an analyte of interest is in a dry or solid sample, as described above), it can be extracted, suspended, or dissolved into a fluid sample first. For example, if an analyte of interest is a nucleic acid, it can be extracted from cells of interest into a solution (e.g., an aqueous solution, such as the buffer described below); in another example, if an analyte of interest is a powder or particulate material (e.g., a powder, a particulate, a soil sample, or spores), it can be suspended or dissolved into a solution (e.g., an aqueous solution, such as the buffer described below) such as by obtaining a sample of the dry material (e.g., using a swab or other instrument) and placing the sample of dry material into the solution. Thus, a fluid sample can refer not only to a liquid sample to be assessed for an analyte of interest, but also to a fluid sample in which a solid material (to be assessed for an analyte of interest) is extracted, suspended or dissolved.

An analyte binding agent, as used herein, refers to second member of a binding pair as described above. Each analyte binding agent is a compound that specifically binds to its analyte of interest (the first member of the binding pair), such as an antibody, a hapten or drug conjugate, a receptor, or another binding partner. In a preferred embodiment, an analyte binding agent is an antibody to its analyte of interest.

Sandwich Assays

The sandwich assay of the invention can utilize a solid phase apparatus. In one embodiment, the solid phase apparatus is a lateral flow solid phase apparatus. In the other embodiment, the solid phase apparatus is a capillary flow solid phase apparatus.

The lateral flow solid phase apparatus can be any solid phase apparatus designed for a lateral flow assay, such as the RAMP™ apparatus (Response Biomedical, Burnaby, British Columbia, Canada; see, e.g., apparatus described in U.S. Pat. Nos. 6,509,196; 7,175,992). Generally, the lateral flow solid phase apparatus includes a membrane through which the test sample will flow. The membrane can be made of a substance having the following characteristics: sufficient porosity to allow capillary action of fluid along its surface and through its interior; the ability to allow movement of coated particles (e.g., analyte binding particles, as described below) or complexes of particles and analyte of interest (e.g., contacted analyte binding particles, as described below) by capillary action (i.e., it must not block the particles or complexes of particles and analyte of interest); and the ability to be wet by the fluid containing the analyte (e.g., hydrophilicity for aqueous fluids, hydrophobicity for organic solvents). Hydrophobicity of a membrane can be altered to render the membrane hydrophilic for use with aqueous fluid, by processes such as those described in U.S. Pat. No. 4,340,482, or U.S. Pat. No. 4,618,533, which describe transformation of a hydrophobic surface into a hydrophilic surface. Examples of membrane substances include: cellulose, cellulose nitrate, cellulose acetate, glass fiber, nylon, polyelectrolyte ion exchange membrane, acrylic copolymer/nylon, and polyethersulfone. In a preferred embodiment, the membrane is made of cellulose nitrate (e.g., a cellulose nitrate membrane with a Mylar backing). The lateral flow solid phase apparatus can also optionally include other features, including sample pads, wicking pads, internal standard components, control components, or other features.

The capillary flow solid phase apparatus can be any solid phase apparatus designed for a capillary flow assay, such as the BioSite Triage® immunoassay products (BioSite Inc., San Diego, Calif.). Generally, the capillary flow solid phase apparatus includes a capillary channel through which the test sample will flow.

Whether a lateral flow solid phase apparatus or a capillary flow solid phase apparatus is used, the solid phase apparatus has an application point, two or more sample capture zones, and a control capture zone. The application point (or application area) is the position on the membrane or in the capillary channel where a fluid can be applied. An application pad can also optionally be used; the application pad rests on the solid phase, immediately adjacent to or covering the application point. The application pad can be made of an absorbent substance which can deliver a fluid sample, when applied to the pad, to the application point on the membrane or on the capillary channel. Representative substances include cellulose, cellulose nitrate, cellulose acetate, nylon, poyelectrolyte ion exchange membrane, acrylic copolymer/nylon, polyethersulfone, or glass fibers. In one embodiment, the pad is a Hemasep®-V pad (Pall Corporation). In another embodiment, the pad is a glass fiber pad. If a wicking pad is present, it can similarly be made from such absorbent substances.

A sample capture zone refers to a point on the membrane or in the capillary channel at which a sample capture reagent is adsorbed (e.g., coated on and/or permeated through the membrane, or coated on the surface of the capillary channel). As used herein, the term "adsorbed" indicates that the agent is immobilized or adhered by non-covalent interactions, in contrast to covalent linkage where chemical means are used to generate an irreversible chemical bond of shared electrons between two linked molecules. Incremental movement (e.g., desorbtion) of an agent that is adsorbed onto a membrane or in a capillary channel may occur, but will have negligible affect on the assays of the invention.

A sample capture reagent is an analyte binding agent, such as those described above, for a particular analyte of interest. A sample capture reagent need not be the same analyte binding agent as described in relation to analyte binding agents on particles, below; however, each sample capture reagent also forms a binding pair with its analyte of interest, in that it specifically and preferentially binds to its analyte of interest. In a preferred embodiment, a sample capture reagent is an antibody directed against its analyte of interest; it can be directed against the same epitope of the analyte as, or against a different epitope of the analyte from, the epitope that binds to the antibodies used as analyte binding agents coated on the particles. Because there is more than one analyte of interest, there will accordingly be more than one sample capture zone—one sample capture zone corresponding to each analyte of interest. Each sample capture zone has at least one sample capture reagent adsorbed thereon, in which the sample capture reagent is an analyte binding agent for its particular (corresponding) analyte of interest. More than one sample capture reagent can be present at each sample capture zone, if desired, provided that all of the sample capture reagents at a particular sample capture zone target the same analyte of interest (although not necessarily the same epitope of that analyte of interest). More than one sample capture reagent can be used at each sample capture zone, if desired.

The apparatus additionally includes a control capture reagent adsorbed in a control capture zone. The control capture reagent is a reagent which reacts with analyte binding particles, but which does not interact with any of the analytes to be measured: for example, the control capture reagent can react with analyte binding agent on analyte binding agent-coated particles; with another material on the particles; or with the particles themselves. For example, if the analyte binding agent is an antibody, the control capture reagent can be an anti-immunoglobulin antibody. In a preferred embodiment, each analyte binding agent is an antibody, and the control capture reagent is an anti-immunoglobulin antibody. The control capture reagent is adsorbed on the solid phase apparatus (coated on and/or permeated in the membrane, or coated in a capillary channel) in a control capture zone.

In certain embodiments, the sample capture zones are positioned sequentially with respect to the flow of liquid by capillary action on the solid phase apparatus, and proximal to the application point. In certain other embodiments, the sample capture zones are approximately equidistant from the application point (e.g., parallel to one another, radially dispersed, or otherwise positioned such that the sample capture zones are proximal to the application point with respect to the flow of liquid). If desired, the sample capture zones can be comparatively closer to the distal end of the solid phase apparatus than to the application point. In a further embodiment, the sample capture zones overlap or occupy the same area; in such an embodiment, the particles used (as described below) are distinctively labeled (i.e., labeled in such a manner that they can be separately identified, such as by differing optical densities, different chemiluminescent markers, and/or different fluorescent markers).

In sequential placement of the sample capture zones in embodiments in which the sample capture zones do not overlap or occupy the same area, the distance between each zone can be varied; all that is required is that the distance is sufficient such that the zones do not overlap. In a preferred embodiment, sequential zones are spaced such that a background level can also be determined between the various zones, as discussed in detail below. Each sample capture zone is approximately equidistant from the sample capture zones adjacent to it. In a particular embodiment, "approximately equidistant" indicates that the distance is as close as possible using standard manufacturing equipment: for example, if the manufacturing equipment resolution is a millimeter, approximately equidistant would be within 1 mm. Alternatively, in another particular embodiment, approximately equidistant resolution can be related to the distance from the center of the first sample capture zone to the center of the second capture zone: for example, the difference between the distance from the center of the first sample capture zone to the center of the second sample capture zone and the distance from the center of the second sample capture zone to the center of the third capture zone, is within 10%, preferably within 7%, preferably within 5%, more preferably within 4%, more preferably within 3%, even more preferably within 2%, and even more preferably within 1%, of the length of the distance from the center of the application point to the center of a sample capture zone (the length of the pathway).

The sample capture zones and the control capture zone are separated from the application point by a space that is sufficiently large to retard the speed of the capillary front to a rate that is slow enough to allow capture of particles when the capillary front reaches the first sample capture zone. In addition, the distance must be sufficiently large so that the total time of migration (movement of the capillary front through the entire solid phase apparatus) is long enough to allow free analyte in a fluid sample to bind to analyte binding particles. The optimal distances between the components on the solid phase apparatus can be determined and adjusted using routine experimentation.

The quantitative assay additionally uses a sample collection apparatus. A sample collection apparatus, as used herein, refers to an apparatus that can be used for collection of the fluid sample or into which a collected fluid sample can be deposited or stored. The sample collection apparatus can be any apparatus which can contain the analyte binding particles, as described below, and which to which can be added a measured volume of fluid sample. Representative sample collection apparatus include a sample tube, a test tube, a vial, a pipette or pipette tip, or a syringe. In a preferred embodiment, the sample collection apparatus is a pipette or pipette tip.

In one embodiment, the sample collection apparatus contains a population of analyte binding particles which are coated with an analyte binding agent for each analyte of interest: for example, a first analyte binding agent for a first analyte of interest; a second analyte binding agent for a second analyte of interest; etc., such that there is an analyte binding agent corresponding to each analyte of interest. Alternatively, the sample collection apparatus can contain a population of analyte binding particles for each analyte binding agent; that is, a population of analyte binding particles for a first analyte of interest; a population of analyte binding particles for a second analyte of interest; etc., such that there is a population of analyte binding particles corresponding to each analyte of interest. If desired, a combination of different types of populations of analyte binding particles can also be used.

The population(s) of particles varies, depending on the size and composition of the particles, the composition of the solid phase apparatus, and the level of sensitivity of the assay. The population typically ranges approximately between $1 \times 10^3$ and $1 \times 10^9$, although fewer or more can be used if desired. In a preferred embodiment, the population is approximately $2 \times 10^8$ particles. The population may be accordingly increased if desired (e.g., with three times as many particles if three analytes of interest are assessed).

Analyte binding particles are particles which can be coated with the analyte binding agent (the second member of the binding pair) for each analyte of interest. In a preferred embodiment, the analyte binding particles are liposomes, colloidal gold, organic polymer latex particles, inorganic fluorescent particles or phosphorescent particles. In a particularly preferred embodiment, the particles are polystyrene latex beads, and most particularly, polystyrene latex beads that have been prepared in the absence of surfactant, such as surfactant free Superactive Uniform Aldehyde/Sulfate Latexes (Interfacial Dynamics Corp., Portland, Oreg.).

The size of the particles is related to porosity of the membrane or the size of the capillary channels, and also to the size of the analytes of interest (e.g., for particulate analytes): the particles must be sufficiently small to be transported along the membrane or through the capillary channel by capillary action of fluid, and also (for solid, e.g., particulate analytes) sufficiently small for the complex of contacted analyte binding particles, as described below, to be transported along the membrane or through the capillary channel by capillary action. The particles can be labeled to facilitate detection. The particles are labeled by a means which does not significantly affect the physical properties of the particles; for example, the particles are labeled internally (that is, the label is included within the particle, such as within the liposome or inside the polystyrene latex bead). Representative labels include luminescent labels; chemiluminescent labels; phosphorescent labels; enzyme-linked labels; chemical labels, such as electroactive agents (e.g., ferrocyanide); and calorimetric labels, such as dyes or fluorescent labels. In one embodiment, a fluorescent label is used. In another embodiment, phosphorescent particles are used, particularly "up-converting" phosphorescent particles, such as those described in U.S. Pat. No. 5,043,265. If the sample capture zones are separate, for example, the same type of label can be used for each population of analyte binding particles (e.g., for both the population of particles for the first analyte of interest, and the population of particles for the second analyte of interest). Alternatively, different types of labels (distinctive labels) can be used, e.g., if the sample capture zones over lap or occupy the same area.

The particles are coated with an analyte binding agent that is a second member of the binding pair for each analyte of interest (e.g., particles having more than one type of analyte binding agent coated thereon; or different populations of particles, each population having a single type of analyte binding agent for its analyte coated thereon). As described above, an analyte binding agent (second member of a binding pair) specifically and preferentially binds to its analyte of interest (first member of the binding pair). Representative analyte binding agents include antibodies (or fragments thereof); haptens; drug conjugates; receptors; or other binding partners. In one preferred embodiment, the analyte binding agent is an antibody to the analyte of interest. Antibodies can be monoclonal antibodies or polyclonal antibodies. The term "antibody", as used herein, also refers to antibody fragments which are sufficient to bind to the analyte of interest. Alternatively, in another embodiment, molecules which specifically bind to the analyte of interest, such as engineered proteins having analyte binding sites, can also be used (Holliger, P. and H. R. Hoogenbloom, *Trends in Biotechnology* 13:7 9 (1995); Chamow, S. M. and A. Ashkenazi, *Trends in Biotechnology* 14:52 60:1996)). In still another embodiment, if the analyte of interest is a drug, a hapten or other drug conjugate can be used as the analyte binding agent. Alternatively, in a further embodiment, a receptor which binds to the analyte can be used (e.g., if the analyte of interest is a ligand). If the analyte is an antibody of known specificity, the particles can be coated with the antigen against which the analyte antibody is directed, or can be coated with antibody to the analyte-antibody. Furthermore, because the analyte and the analyte binding agent form a binding pair, compounds or molecules described as representative analytes can also serve as analyte binding agents, and those described as representative analyte binding agents can similarly serve as analytes, as described herein.

The analyte binding particles contained within the sample collection apparatus are stored in a stable form within the sample collection apparatus. A "stable form," as the term is used herein, indicates a form in which the particles do not significantly change in chemical makeup or physical state during storage. The stable form can be a liquid, gel, or solid form. In preferred embodiments, the analyte binding particles contained within the sample collection apparatus are evaporatively dried; freeze-dried; and/or vacuum-dried.

In a particularly preferred embodiment, the sample collection apparatus is a pipette tip in which are vacuum-dried analyte binding particles.

To perform the assay, a fluid sample to be assessed for the presence of the analytes of interest, as described above, is used. In one embodiment, the fluid sample is introduced into (drawn into, poured into, or otherwise placed into) the sample collection apparatus. For example, in one embodiment, the fluid sample is drawn up into a sample collection apparatus that comprises a pipette tip. Introduction of the fluid sample into the sample collection apparatus results in mixing of the fluid sample with the analyte binding particles, forming a "mixed fluid sample." If the analyte binding particles are evaporatively-, freeze- or vacuum-dried, the introduction of the fluid sample into the sample collection apparatus can result in rehydration and suspension of the analyte binding particles in the fluid sample. A buffer (e.g, for dilution) is also introduced into the mixed fluid sample, forming a "buffered, mixed fluid sample." The buffered, mixed fluid sample can be formed either by dispensing the mixed fluid sample into a "buffer container" (e.g., test tube) containing the buffer, or by introducing the buffer into the sample collection apparatus prior to introducing the fluid sample. Alternatively, if the analyte of interest is a solid (e.g., a powder, a particulate; spore; or other particle, as described above), the fluid sample as described above can be prepared by introducing the solid into the buffer container; in this embodiment, the buffered, mixed fluid sample is formed by introducing the fluid sample (comprising the buffer) into the sample collection apparatus. In another embodiment, the buffer is introduced into the sample collection apparatus, followed by introduction of the fluid sample into the sample collection apparatus.

The buffer can be an aqueous fluid that supports a reaction between the analyte of interest and the analyte binding agent (e.g., does not interfere with antibody/antigen interaction); and that has a viscosity that is sufficiently low to allow movement of the fluid by capillary action. In one embodiment, the buffer contains one or more of the following components: a buffering agent (e.g., phosphate); a salt (e.g., NaCl); a protein stabilizer (e.g., BSA, casein, serum); and/or a detergent such as a nonionic detergent or a surfactant (e.g., one or more of the following agents commonly available in surfactant tool kits: NINATE 411, Zonyl FSN 100, Aerosol OT 100%, GEROPON T 77, BIO TERGE AS 40, STANDAPOL ES 1, Tetronic 1307, Surffiyol 465, Surfynol 485, Surfynol 104PG 50, IGEPAL CA210, TRITON X 45, TRITON X 100, TRI- TON X305, SILWET L7600, RHODASURF ON 870, Cremophor EL, TWEEN 20, TWEEN 80, BRIJ 35, CHEMAL LA 9, Pluronic L64, SURFACTANT 10G, SPAN 60, CREL). Optionally, if desired, the buffer can contain a thickening agent. Such components for buffers are commercially available. Representative buffers include, for example, saline, or 50 mM Tris HCl, pH 7.2. Alternatively, water can be used in lieu of a buffered solution; as used herein, the term "buffer" refers to either a buffered solution or to water. In another embodiment, the components of the buffer are lyophilized and included in the sample collection apparatus; in this embodiment, water is used in lieu of the buffered solution in the methods of the invention.

To disperse the analyte binding particles further into the fluid sample, if desired, the sample collection apparatus into which the fluid sample and the buffer has been introduced, or the buffer container into which the mixed fluid sample has been introduced, can be agitated (e.g., vortexed, shaken, pipetted down and up, etc.).

In a preferred embodiment, the sample collection apparatus comprises a pipette tip having vacuum-dried analyte binding particles within its tip; the fluid sample is drawn into the pipette, thereby rehydrating the dried analyte binding particles and forming a mixed fluid sample. In a particularly preferred embodiment, the mixed fluid sample is introduced into a buffer container, resulting in a buffered mixed fluid sample; the buffered mixed fluid sample in the buffer container is pipetted up and down using the sample collection apparatus, thereby further dispersing the analyte binding particles.

If an analyte of interest is present in the buffered, mixed fluid sample, binding occurs between that analyte and its analyte binding particles. "Binding" of analyte to analyte binding particles indicates that an analyte binding agent coated onto the particle is interacting with (e.g., binding to) its analyte of interest. Analyte binding particles which have been maintained (incubated) under conditions allowing analytes in the fluid (if present) to bind to analyte binding particles adsorbed in the contact region are referred to herein as "contacted analyte binding particles". Contacted analyte binding particles may or may not have analytes bound to the analyte binding agent, depending on whether or not each analyte of interest is present in the fluid sample and whether analyte has bound to the analyte binding agent on the analyte binding particles. Because there are multiple binding sites for analyte on analyte binding particles, the presence and the concentration of analyte bound to analyte binding particles varies; the concentration of an analyte bound to analyte binding particles increases proportionally with the amount of analyte present in the fluid sample, and the probability of an analyte binding particle being arrested in the corresponding sample capture zone (as described below) similarly increases with increasing amount of analyte bound to the analyte binding particles. Thus, the population of contacted analyte binding particles may comprise particles having various amount of analytes bound to the analyte binding agents, as well as particles having no analytes bound to the analyte binding agents Oust as the analyte binding particles initially have no analyte bound to the analyte binding agent). Furthermore, the degree of binding increases as the time factor of the conditions increases: while the majority of binding occurs within one minute (e.g., 60 seconds, preferably less than 60 seconds (e.g., 45 seconds, 30 seconds, or less), additional incubation (e.g., more than one minute (2 minutes, 5 minutes, 10 minutes, 15 minutes) results in additional binding. If there is more than one population of analyte binding particles (e.g., separate populations for the different analytes of interest), analyte binding particles which have been maintained (incubated) under conditions allowing analytes in the fluid (if present) to bind to the analyte binding particles are referred to as "contacted first analyte binding particles," "contacted second analyte binding particles," etc., for each analyte of interest, and are collectively known as contacted analyte binding particles.

The buffered, mixed fluid sample is applied to the application point of the solid phase apparatus, or to the application pad, if present. After the solid phase apparatus is contacted with the buffered, mixed fluid sample, the solid phase apparatus is maintained under conditions which allow fluid to move by capillary action to and through the apparatus. Contacted analyte binding particles move as a result of capillary action of the fluid from the buffered, mixed fluid sample. The solid phase apparatus is maintained under conditions (e.g., sufficient time and fluid volume) which allow contacted analyte binding particles to move by capillary action to and through the sample capture zones and to and through the control capture zone, and optionally also to allow movement subsequently beyond the capture zone(s) (e.g., into a wicking pad), thereby removing any non-bound particles from the capture zones.

The movement of some of the contacted analyte binding particles is arrested by binding of contacted analyte binding particles to the sample capture reagent in the sample capture zone for each analyte of interest, and by binding of some of the contacted analyte binding particles to the control capture reagent in the control capture zone. In one preferred embodiment, the analyte binding agent(s) is antibody to the antigen of interest, and the control capture reagent can be antibody against immunoglobulin of the species from which the analyte binding agent is derived. In this embodiment, the antibody to immunoglobulin should be non-cross reactive with other components of the sample: for example, if a human sample is being tested, an antibody that does not react with human immunoglobulin can be used as the control capture reagent.

Sample capture reagent binds to contacted analyte binding particles by binding to analyte of interest which is bound to analyte binding agent on the contacted analyte binding particles. The term, sample-reagent particle complexes, as used herein, refers to a complex of sample capture reagent and contacted analyte binding particles. Contacted analyte binding particles are arrested in the sample capture zones, forming the sample-reagent-particle complexes, due to capture of contacted analyte binding particles by interaction of analyte with sample capture reagent in the sample capture zone. Each sample capture zone may have sample-reagent-particle complexes arrested therein, depending on whether each particular analyte of interest is present in the sample and has bound to its analyte binding agent on contacted analyte binding particles.

Control capture reagent binds to contacted analyte binding particles by binding to analyte binding agent on the contacted analyte binding particles. The term, control-reagent-particle complexes, as used herein, refers to a complex of the control capture reagent and contacted analyte binding particles. Contacted analyte binding particles are arrested in the control capture zone, forming the control-reagent-particle complexes, due to capture of contacted analyte binding particles by interaction of analyte binding particles with control capture reagent in the control capture zone. As indicated above, the control capture reagent interacts with analyte binding particles (e.g., with the analyte binding agent on the analyte binding agent-coated particles, or another material on the particles, or with the particles themselves), but not with any of the analytes used in the test (for which there are sample capture zones) themselves.

Typically, capillary action subsequently moves any contacted analyte binding particles that have not been arrested in either a sample capture zone or the control capture zone, onwards beyond these zones, thereby removing any particles that have not been arrested. In a preferred embodiment, the fluid moves any contacted analyte binding particles that have not been arrested, into a wicking pad which follows the capture zone(s).

If desired, a secondary wash step can be used. A buffer (e.g., the buffer described above) can be applied at the application point after the buffered, mixed fluid sample has soaked in to the membrane, been drawn through the capillary tube, or soaked into the application pad, if present. The secondary wash step can be used at any time thereafter, provided that it does not dilute the buffered, mixed fluid sample. A secondary wash step can contribute to reduction of background signal when the analyte binding particles are detected, as described below.

The amount of analyte binding particles arrested in each sample capture zone (sample-reagent-particle complexes) is then detected using an appropriate means for the type of label used on the analyte binding particles. In a preferred embodiment, the amount is detected by an optical method, such as by measuring the amount of fluorescence of the label of the analyte binding particles.

In a particularly preferred embodiment, the entire area from upstream of the first sample capture zone to beyond the control capture zone is scanned so that several hundred measurements are taken along the direction of liquid flow. In this manner the amount of binding at each zone and between the zones and before the initial zone and after the control zone can be determined with enough resolution to quantitate the amount of label in each of these areas. The amount of binding between the zones can be used to correct for background signal, as described below.

Alternatively, the amount of sample-reagent-particle complexes can be detected using electrical conductivity or dielectric (capacitance). Alternatively, electrochemical detection of released electroactive agents, such as indium, bismuth, gallium or tellurium ions, as described by Hayes et al. (*Analytical Chem.* 66:1860-1865 (1994)) or ferrocyanide as suggested by Roberts and Durst (*Analytical Chem.* 67:482-491 (1995)) can be used. For example, if liposomes are used, ferrocyanide encapsulated within the liposome can be released by addition of a drop of detergent at the capture zone, and the released ferrocyanide detected electrochemically (Roberts and Durst, id.). If chelating agent-protein conjugates are used to chelate metal ions, addition of a drop of acid at the capture zone will release the ions and allow quantitation by anodic stripping voltametry (Hayes et al., id.). Similarly, the amount of analyte binding particles arrested in the control capture zone (also referred to herein as "the control") is detected in the same manner as the amount of analyte binding particles in a sample capture zone.

A corrected analyte binding particle amount for each analyte of interest is then determined. A corrected analyte binding particle amount is based on the amount of analyte binding particles arrested in the sample capture zone corresponding to analyte of interest, and in the other sample capture zones as well as the control capture zone. For example, in one embodiment, the corrected analyte binding particle amount for the first analyte of interest is determined as a ratio (R) of the analyte binding particle amount present in the first sample capture zone to the sum of the analyte binding particle amounts present in that first sample capture zone plus the amount present in each of the other sample capture zones and in the control capture zone. In one embodiment, for example, if there are two analytes of interest, the corrected analyte binding particle amount for the first analyte of interest is determined from the ratio of: the amount of analyte binding particles present in the first sample capture zone, to the sum of (the amount of analyte binding particles present in the first sample capture zone, plus the amount of analyte binding particles present in the second sample capture zone, plus the amount of analyte binding particles present in the control capture zone). Similarly, for two analytes of interest, the corrected analyte binding particle amount for the second analyte of interest is determined from the ratio of: the amount of analyte binding particles present in the second sample capture zone, to the sum of (the amount of analyte binding particles present in the first sample capture zone, plus the amount of analyte binding particles present in the second sample capture zone, plus the amount of analyte binding particles present in the control capture zone).

Once the corrected analyte binding particle amount for each analyte of interest is determined, the presence or absence of an analyte of interest can then be determined from the corrected analyte binding particle amount for that analyte using appropriate comparison. In one embodiment, the corrected analyte binding particle amount for each analyte of interest is compared to a threshold value that is previously determined from a standard curve having an established relationship between the corrected binding particle amount and known concentrations of the analyte; a corrected analyte binding particle amount that is equal to or greater than the threshold value, is indicative of a positive result (i.e., is indicative of the presence of that analyte of interest in the test sample), and a corrected analyte binding particle amount that is less than the threshold value, is indicative of a negative result (i.e., is indicative of the absence of that analyte of interest in the test sample).

Alternatively, once the corrected analyte binding particle amount for each analyte of interest is determined, the amount of an analyte of interest can then be determined from the corrected analyte binding particle amount for that analyte using appropriate calculation. For example, the amount of analyte present can be directly related the corrected analyte binding particle amount (the ratio), utilizing a standard curve. The standard curve is generated by preparing a series of control samples, containing known concentrations of the analyte of interest in the fluid in which the analyte is to be detected (for example, such as serum depleted of the analyte). The assay is then performed on the series of control samples; the value of R is measured for each control sample; and the R values are plotted as a function of the concentration of analyte included in the control sample. Samples containing an unknown amount of analyte (the "test samples") are assayed by measuring the value of R for the test sample, and the concentration of analyte in the test sample is determined by referring to the standard curve. As above, one standard curve can be generated and used for all test samples in a lot (e.g., for all test samples using a specified preparation of test reagents); it is not necessary that the standard curve be re generated for each test sample. Alternatively, other ratios and/or standard curves can also be used to determine the amount of analyte in the sample.

In addition, if desired, the amount of label that is present in the background can be subtracted from the analyte binding particle amount present in each sample capture zone and from the analyte binding particle amount present in the control capture zone during calculation of the corrected analyte binding particle amount and prior to calculation of the ratio (R). For example, after the assay is run (liquid has moved through and beyond the capture zones), the whole, or part, of the solid phase apparatus can be scanned to assess the quantity of labeled particles in the areas before, in, and after each of the capture zones. The scan can be done primarily around the area which includes the capture zones, but can also be performed on the area extending outside and/or between these zones. The particles present in areas outside the capture zones are "background"—that is, particles that bind non-specifically to the solid phase apparatus in the presence of the sample and other constituents in the sample matrix which are also present at the capture zones. The amount of particles present in the capture zone includes this non-specific background in addition to the specific particles captured by the capture reagent. The detected background amount of particles (i.e., the amount of particles detected in a location outside the capture zone, such as before and/or after that capture zone) can be subtracted from the total amount of particles determined in an individual capture zone. This corrects for the background amount, and can yield more accurate determination of the amount of analyte present in the sample. For example, a detected background amount can be identified in a location immediately adjacent and upstream of a capture zone; or in a location immediately adjacent and downstream of a capture zone; or between the application point and the first sample capture zone; or in another location besides the capture zones. Alternatively, a detected background amount can be identified in more than one location: for example, a detected background amount can be identified in a location upstream of a capture zone, and also downstream of the same capture zone; an average of these two detected background amounts can be used as the detected background particle amount that is subtracted from the analyte binding particle amount to yield the "background-corrected analyte binding particle amount." A "background-corrected analyte binding particle amount," as used herein, refers to an analyte binding particle amount from which a background amount of particles has been subtracted.

In a preferred embodiment, the detected background particle amount is determined immediately adjacent and upstream of each individual capture zone: for example, in an embodiment in which there are two analytes of interest and thus two sample capture zones, the background amount is detected upstream of the first sample capture zone (for the first sample capture zone); downstream of the first sample capture zone and upstream of the second sample capture zone (for the second sample capture zone); and downstream of the second sample capture zone and upstream of the control capture zone (for the control capture zone). Alternatively, the same detected background amount can be used for each of the sample capture zones and for the control capture zone.

In another preferred embodiment, a detected background particle amount is determined both immediately adjacent and upstream of each individual capture zone, as well as immediately adjacent and downstream of each individual capture zone, and an average of the two amounts is used in the determination of the background-corrected analyte binding particle amount. For example, in an embodiment in which there are two analytes of interest and thus two sample capture zones, the background amount is detected upstream of the first sample capture zone and downstream of the first sample capture zone, and these two amounts are averaged and used as the background amount for the first sample capture zone; the background amount that is downstream of the first sample capture zone is also used as a background amount that is upstream of the second sample capture zone, and it is averaged with a background amount that is downstream of the second sample capture zone, so that the average can be used as the background amount for the second sample capture zone; etc. Other combinations of readings can be used and averaged to serve as the background amount, if desired.

In one preferred embodiment of the invention, the two analytes of interest are influenza A and influenza B. In this embodiment, antibodies to influenza A are used as the first analyte binding agent, and antibodies to influenza B are used as the second analyte binding agent.

"Competitive" or "Inhibition" Assays

The competitive or inhibition assay of the invention, like the sandwich assays, utilizes a solid phase apparatus, as described above, that includes an application point, two or more sample capture zones, and a control capture zone. This embodiment also utilizes a sample collection apparatus, as described above. The sample collection apparatus for the competitive (inhibition) assay contains a population of analyte coated particles which are coated with all of the analytes of interest (in lieu of being coated with an analyte binding agents, as described for the sandwich assays) or with analogs of all of the analyte of interest; alternatively, the sample collection apparatus contains more than one population of analyte coated particles (with one population for each analyte of interest); each population is coated with an analyte of interest or with an analog of an analyte of interest, or a combination thereof An analog of the analyte, as used herein, is a compound that has similar binding characteristics as the analyte, in that is forms a binding pair with the analyte-binding agent as described above. The analyte and/or analog of the analyte can be coated directly on the particles, or can be indirectly bound to the particles. As used below, the term analyte coated particles can refer to particles that are coated either with an analyte of interest and/or with an analog of an analyte of interest. As above with regard to the sandwich assay, the population of particles varies, depending on the size and composition of the particles, the composition of the solid phase apparatus, and the level of sensitivity of the assay.

As above, the sample capture zones are locations on the solid phase apparatus at which a sample capture reagent is adsorbed. The sample capture reagent is an analyte binding agent, such as those described above. The sample capture reagent need not be the same analyte binding agent as described above; however, the sample capture reagent also forms a binding pair with the analyte of interest, in that it specifically and preferentially binds to an analyte of interest. Because there is more than one analyte of interest, there will be more than one sample capture zone, as above. As above, in a preferred embodiment, the sample capture reagent is an antibody directed against the analyte; it can be directed against the same epitope of the analyte as, or against a different epitope of the analyte from, the epitope that binds to the antibodies used as analyte binding agents coated on the particles. More than one sample capture reagent can be used at each sample capture zone, if desired.

The apparatus additionally includes a control capture reagent, as described above, that reacts with the analyte coated particles, but does not interact with the analyte to be measured: for example, the control capture reagent can react with another material on the particles (e.g., a carrier for the analyte that is bound to the particles; an antibody); or with the particles themselves. In a preferred embodiment, the sample capture reagent and the control capture agent are both antibodies. The control capture reagent is adsorbed in the control capture zone. The components of the competitive assay are positioned in a similar manner as described above with regard to the sandwich assay.

To perform the competitive assay, a fluid sample to be assessed for the presence of the analytes of interest, as described above, is used. In one embodiment, the fluid sample is introduced into (drawn into, poured into, or otherwise placed into) the sample collection apparatus. For example, in one embodiment, the fluid sample is drawn up into a sample collection apparatus that comprises a pipette tip. Introduction of the fluid sample into the sample collection apparatus results in mixing of the fluid sample with the analyte coated particles, forming a mixed fluid sample. If the analyte coated particles are evaporatively-, freeze- or vacuum-dried, the introduction of the fluid sample into the sample collection apparatus can result in rehydration and suspension of the analyte binding particles in the fluid sample. A buffer (e.g., as described above) is also introduced into the mixed fluid sample, forming a buffered, mixed fluid sample. The buffered, mixed fluid sample can be formed either by dispensing the mixed fluid sample into a buffer container (e.g., test tube) containing the buffer, or by introducing the buffer into the sample collection apparatus prior to introducing the fluid sample. In another embodiment, the buffer is introduced into the sample collection apparatus, followed by introduction of the fluid sample into the sample collection apparatus. Alternatively, if analyte of interest is a solid (e.g., a powder, a particulate; spore; or other particle, as described above), the fluid sample as described above can be prepared by introducing the solid into the buffer container; in this embodiment, the buffered, mixed fluid sample is formed by introducing the fluid sample (comprising the buffer) into the sample collection apparatus.

To disperse the analyte coated particles further into the fluid sample, if desired, the sample collection apparatus into which the fluid sample and the buffer has been introduced, or the buffer container into which the mixed fluid sample has been introduced, can be agitated (e.g., vortexed, shaken, pipetted down and up, etc.).

In a preferred embodiment, the sample collection apparatus comprises a pipette tip having vacuum-dried analyte coated particles within its tip; the fluid sample is drawn into the pipette, thereby rehydrating the dried analyte coated particles and forming a mixed fluid sample. In a particularly preferred embodiment, the mixed fluid sample is introduced into a buffer container, resulting in a buffered mixed fluid sample; the buffered mixed fluid sample in the buffer container is pipetted up and down using the sample collection apparatus, thereby further dispersing the analyte coated particles.

The buffered, mixed fluid sample is applied to the application point of the solid phase apparatus, or to the application pad, if present. After the solid phase apparatus is contacted with the buffered, mixed fluid sample, the apparatus is maintained under conditions which allow fluid to move by capillary action to and through the solid phase apparatus. The analyte coated particles (and analyte, if present in the sample) move through the apparatus as a result of capillary action of the fluid from the buffered, mixed fluid sample, to and through the sample capture zones and to and through the control capture zone.

The movement of some of the analyte coated particles is arrested by binding of analyte coated particles to the sample capture reagent in the sample capture zones, and also by binding of some of the analyte coated particles to the control capture reagent in the control capture zone. The analyte coated particles compete with analyte (if present) in the sample for binding to the sample capture reagent. The sample capture reagent binds to analyte coated particles by binding to analyte on the analyte coated particles. The term, sample-reagent-analyte coated particle complexes, as used herein, refers to a complex of the sample capture reagent and analyte coated particles. The analyte coated particles are arrested in a sample capture zone, forming the sample-reagent-analyte coated-particle complexes, due to capture of the analyte coated particles by interaction of the analyte of interest on the particles with the sample capture reagent in the sample capture zone.

The control capture reagent binds to analyte coated particles by binding to any component of the analyte coated particles except the analyte itself. The term, control-reagent-analyte coated particle complexes, as used above, refers to a complex of the control capture reagent and analyte coated particles. As above, the analyte coated particles are arrested in the control capture zone, forming the control-reagent-analyte coated particle complexes, due to capture of the analyte coated particles by interaction of the analyte binding particles with the control capture reagent in the control capture zone.

Capillary action can subsequently moves any analyte coated particles that have not been arrested in either a sample capture zone or the control capture zone, onwards beyond the capture zones.

The analyte coated particles arrested in each capture zone is then detected. The analyte coated particles are detected using an appropriate means for the type of label used on the analyte coated particles, as is described above in relation to detection of amounts of analyte binding particles in the sandwich assay. Similarly, the amount of analyte coated particles arrested in the control capture zone (also referred to herein as "the control") is detected in the same manner as the amount of analyte coated particles in a sample capture zones.

A corrected analyte coated particle amount for each analyte of interest is then determined. A corrected analyte coated particle amount is based on the amount of analyte coated particles arrested in the sample capture zone corresponding to analyte of interest, and in the other sample capture zones as well as the control capture zone. For example, in one embodiment, the corrected analyte coated particle amount for the first analyte of interest is inversely related to a ratio (R) of the analyte coated particle amount present in the first sample capture zone to the sum of the analyte coated particle amounts present in that first sample capture zone plus the amount present in each of the other sample capture zones and in the control capture zone. In one embodiment, for example, if there are two analytes of interest, the corrected analyte coated particle amount for the first analyte of interest is inversely related the ratio of: the amount of analyte coated particles present in the first sample capture zone, to the sum of (the amount of analyte coated particles present in the first sample capture zone, plus the amount of analyte coated particles present in the second sample capture zone, plus the amount of analyte coated particles present in the control capture zone). Similarly, for two analytes of interest, the corrected analyte coated particle amount for the second analyte of interest is inversely related to the ratio of: the amount of analyte coated particles present in the second sample capture zone, to the sum of (the amount of analyte coated particles present in the first sample capture zone, plus the amount of analyte coated particles present in the second sample capture zone, plus the amount of analyte coated particles present in the control capture zone).

Once the corrected analyte coated particle amount for each analyte of interest is determined, the presence or absence of an analyte of interest can then be determined from the corrected analyte coated particle amount for that analyte using appropriate comparison. In one embodiment, the corrected analyte coated particle amount for each analyte of interest is compared to a threshold value that is previously determined, as described above in relation to sandwich" assays; a corrected analyte binding particle amount that is equal to or greater than the threshold value, is indicative of a negative result (i.e., is indicative of the absence of that analyte of interest in the test sample), and a corrected analyte coated particle amount that is more than the threshold value, is indicative of a positive result (i.e., is indicative of the presence of that analyte of interest in the test sample).

Alternatively, once the corrected analyte coated particle amount for each analyte of interest is determined, the amount of an analyte of interest can then be determined from the corrected analyte coated particle amount for that analyte using appropriate calculation. For example, the amount of analyte present can be then determined from the corrected analyte coated particle amount (the ratio), utilizing a standard curve. The standard curve is generated by preparing a series of control samples, containing known concentrations of the analyte of interest in the fluid in which the analyte is to be detected (for example, such as serum depleted of the analyte). The assay is then performed on the series of control samples; the value of R is measured for each control sample; and the R values are plotted as a function of the concentration of analyte included in the control sample. Samples containing an unknown amount of analyte (the "test samples") are assayed by measuring the value of R for the test sample, and the concentration of analyte in the test sample is determined by referring to the standard curve. As above, one standard curve can be generated and used for all test samples in a lot (e.g., for all test samples using a specified preparation of test reagents); it is not necessary that the standard curve be re-generated for each test sample.

Alternatively, other ratios and/or standard curves can also be used to determine the amount of analyte in the sample, as described above.

In addition, if desired, the amount of label that is present in the background can be subtracted from the analyte coated particle amount present in each sample capture zone and from the analyte coated particle amount present in the control capture zone during the calculation of the corrected analyte coated particle amount and prior to calculation of the ratio (R), as described above in relation to sandwich assays. For example, a detected background amount can be identified in a location immediately adjacent and upstream of a capture zone; or in a location immediately adjacent and downstream of a capture zone; or between the application point and the first sample capture zone; or in another location besides the capture zones. Alternatively, a detected background amount can be identified in more than one location: for example, a detected background amount can be identified in a location upstream of a capture zone, and also downstream of the same capture zone; an average of these two detected background amounts can be used as the detected background particle amount that is subtracted from the analyte coated particle amount to yield the "background-corrected analyte coated particle amount." A "background-corrected coated binding particle amount," as used herein, refers to an analyte coated particle amount from which a background amount of particles has been subtracted.

In a preferred embodiment, the detected background particle amount is determined immediately adjacent and upstream of each individual capture zone: for example, in an embodiment in which there are two analytes of interest and thus two sample capture zones, the background amount is detected upstream of the first sample capture zone (for the first sample capture zone); downstream of the first sample capture zone and upstream of the second sample capture zone (for the second sample capture zone); and downstream of the second sample capture zone and upstream of the control capture zone (for the control capture zone). Alternatively, the same detected background amount can be used for each of the sample capture zones and for the control capture zone. In another preferred embodiment, a detected background particle amount is determined both immediately adjacent and upstream of each individual capture zone, as well as immediately adjacent and downstream of each individual capture zone, and an average of the two amounts is used in the determination of the background-corrected analyte coated particle amount. For example, in an embodiment in which there are two analytes of interest and thus two sample capture zones, the background amount is detected upstream of the first sample capture zone and downstream of the first sample capture zone, and these two amounts are averaged and used as the background amount for the first sample capture zone; the background amount that is downstream of the first sample capture zone is also used as a background amount that is upstream of the second sample capture zone, and it is averaged with a background amount that is downstream of the second sample capture zone, so that the average can be used as the background amount for the second sample capture zone; etc. Other combinations of readings can be used and averaged to serve as the background amount, if desired.

Benefits of the Invention

The methods of the invention provide assays with enhanced sensitivity, when compared with assays in which the analyte binding particles are imbedded within a membrane of a solid phase apparatus or contained in a conjugate pad placed in contact with the membrane of the solid phase apparatus, or similarly placed on capillary flow solid phase apparati. For the sandwich assays, for example, because the fluid sample to be assayed for the analyte of interest is mixed with the analyte binding particles prior to application to the solid phase apparatus, there is a longer time for the analyte of interest to bind to the analyte binding particles prior to the capture reaction which occurs on the solid phase. Furthermore, because the interaction between the analyte of interest and the analyte binding particles occurs in the fluid phase, it allows more efficient binding because of greater mobility of the particles, than the same interaction between analyte of interest and analyte binding particles would be in the matrix of the solid phase apparatus. Also, with regard to both the sandwich and the competitive assays, a greater number of particles can be included in a fluid collection apparatus than would be possible to embed in a solid phase apparatus; the greater number further enhances the sensitivity of the reaction. In addition, because the analyte binding particles (or analyte coated particles) are dispersed in the buffered, mixed fluid sample prior to application of the buffered, mixed fluid sample to the solid phase, the particles pass over the capture zones in a continuous manner through the capillary action of the fluid, rather than in a quick wave on the crest of a fluid front. As a result, a lower concentration of particles flows through the capture zones for a longer time: thus the time during which particles can be "captured" is effectively increased, allowing higher specific binding at the capture zones while the amount of particles that pass through the capture zones is effectively lowered, thereby avoiding the non-specific, physical blocking of capture of some particles by others which occurs when the particles pass on the crest of a fluid front.

Furthermore, an assessment can be made for multiple analytes, using a single internal control, thereby facilitating analysis of several compounds concurrently. In addition, use of a ratio provides a correction based on internal calibrators and corrects for variation in the total amounts of particles in the assay, thereby compensating for different amounts of label as well as for differences in sensitivity of the assay.

Although the assays of the invention have been described particularly in relation to immunoassays, the assays can similarly be used with other binding pairs as described above (e.g., nucleic acids, receptor-ligands, lectin-sugars), using the same methods as described above with the desired components as the analyte and the and the analyte binding agent.

Kits of the Invention

The invention also includes kits for use in the methods described herein. Kit components can include: first and/or second members of a specific binding pair, buffers and/or buffer containers, fluid collection means, one or more solid phase apparatus (optionally comprising an application pad and/or wicking pad), at least one sample collection apparatus, one or more buffer containers, control samples for generation of a standard curve and/or other standard curve information, analyte binding particles, analyte coated particles, and/or control particles, capture reagents, antibodies, tools to assist in collecting of samples to be assessed for analyte of interest (e.g., swabs), disposal apparatus (e.g., biohazard waste bags), and/or other information or instructions regarding the sample collection apparatus (e.g., lot information, expiration date, etc.). For example, in one embodiment, a kit comprises at least one sample collection apparatus having analyte binding particles within it; in a preferred embodiment, a kit comprises at least one pipette tip having evaporatively-dried, vacuum-dried or freeze-dried analyte binding particles therein. In another embodiment, a kit comprises at least one solid phase apparatus as described herein and at least one sample collection apparatus. In another preferred embodiment, a kit comprises at least one pipette; at least one or more pipette tips having evaporatively-dried, vacuum-dried or freeze-dried analyte binding particles therein; and at least one solid phase apparatus. This preferred embodiment can also optionally contain information regarding the standard curve, lot information, and/or expiration date relating to the analyte binding particles in the pipette tips. In yet another preferred embodiment, a kit comprises at least one sample collection apparatus; at least one pipette tip having dried analyte binding particles thereon; at least one solid phase apparatus; and at least one buffer container. This preferred embodiment can also optionally contain buffer within the buffer container; and tool (e.g., a swab) for collection of a solid sample.

The invention is illustrated by the following Exemplification, which is not intended to be limiting in any way.

Exemplification: Analysis of Samples for Influenza A and B

A. Materials

To prepare the membrane strips for the immunochromatographic assay, the following procedure is used:

1.5 mg/ml, 1 ul/cm FluA antibody striped at TL-position (first sample capture zone)

1.5 mg/ml, 1 ul/cm FluB antibody striped at UL-position (second sample capture zone)

1 mg/ml, 1 ul/cm Goat anti-mouse antibody striped at ISL-position (control capture zone).

The above antibodies are striped by applying the antibody solutions at the rate of 1 ul/cm on nitrocellulose membrane which is then blocked with 1% PVA, washed with 10 mM PB solution, and then dried. The membrane is cut into 5 mm wide strips.

Test cartridges (solid phase apparati) are assembled using the strips, a sample pad, and a wicking pad, as described herein. To prepare analyte binding particles, one of the following two formats is used:

Format 1: Co-conjugate

Covalently conjugate 0.25 mg of FluA antibody AND 0.125 mg FluB antibody to 4 ml of fluorescent dyed latex beads. Spot the latex-antibody conjugate in a pipet tip (sample collection apparatus) and dry using a vacuum pump to prepare assay tips or include the latex antibody conjugate with sample buffer in lyophilized buffer.

Format 2: Separate Conjugations

Covalently conjugate 0.25 mg of FluA antibody to 4 ml of fluorescent dyed latex beads. Covalently conjugate 0.125 mg FluB antibody to 4 ml of fluorescent dyed latex beads. Combine the FluA antibody-latex conjugate and FluB antibody-latex conjugate and spot the combined conjugates in a pipet tip (sample collection apparatus) and dry using a vacuum pump to prepare assay tips or include the latex antibody conjugate with sample buffer in lyophilized buffer.

To prepare buffer, one of the following two formats is used:

Format 1: Liquid Buffer Format: Sample Buffer composition of 138 mM PB, 138 mM NaCl, 3.6% BSA, 0.84% Surfactant 10G, 0.6% casein, 0.05% Polyox, 0.05% v/v ProClin 300, pH 7.2 for sample buffer. This format utilizes assay tips as described above.

Format 2: Lyophilized Buffer Format: Freeze dry above liquid buffer with or without latex antibody conjugate in lyophilized sample buffer. If latex is included in lyophilized buffer, latex does not need to be dried in pipet tip.

B. Method

Test sample suspected of containing influenza (flu) is prepared in sample buffer as described above (e.g., test sample is diluted by adding directly into liquid sample buffer or the sample is used to reconstitute lyophilized sample buffer). Latex-antibody conjugate is included in lyophilized sample buffer or latex-antibody conjugate is added to the prepared sample by mixing the sample using assay tips. Sample is then added into the test cartridge (A RAMP cartridge, Response Biomedical, Burnaby, Canada) and cartridge inserted in the RAMP Fluorescence Reader (Response Biomedical).

After 14 minutes, the cartridge is scanned using the RAMP Fluorescence Reader. Fluorescence measurements are measured at the UL (first sample capture zone), TL (second sample capture zone), ISL (control capture zone), and corresponding background positions for each of these zones. The UL, TL, and ISL signals are corrected by subtracting the corresponding background signals. Calculation of ratios for the FluA and FluB assays are performed by the reader as follows:

$$\text{Flu}A\ \text{Ratio} = dR10 = TL/(TL+UL+ISL)$$

$$\text{Flu}B\ \text{Ratio} = dUR10 = UL/(TL+UL+ISL)$$

The dR10 and dUR10 ratios are compared to a pre-defined threshold level for each value. If the ratio value is equal to or greater than the threshold level, the result is positive. If the ratio value is less than the threshold level, the result is negative.

Alternately, the calculated ratios can be compared to a pre-defined standard curve and the values could be converted into a quantitative result to measure concentration of the sample.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of measuring an amount of at least two analytes of interest in a test sample, comprising:
   a) providing a solid phase apparatus comprising an application point, at least two sample capture zones, and a control capture zone; the first sample capture zone having a first sample capture reagent adsorbed thereon, the second sample capture zone having a second sample capture reagent adsorbed thereon, and the control capture zone having a control capture reagent adsorbed thereon; wherein the application point, the first sample zone, second capture zone, and control capture zone are sequentially located on the solid phase apparatus;

b) providing a sample collection apparatus containing a population of first analyte binding particles and a population of second analyte binding particles, wherein the first analyte binding particles are coated with a first analyte binding agent and the second analyte binding particles are coated with a second analyte binding agent;

c) either i) introducing the fluid sample into the sample collection apparatus, producing a mixed fluid sample, and subsequently introducing a buffer into the mixed fluid sample; ii) introducing a buffer into the sample collection apparatus and subsequently introducing the fluid sample; or iii) forming the fluid sample by introducing a solid sample into a buffer, and subsequently introducing the fluid sample into the sample collection apparatus, thereby producing a buffered, mixed fluid sample comprising contacted first analyte binding particles and contacted second analyte binding particles;

d) applying the buffered, mixed fluid sample to the application point of the solid phase apparatus;

e) maintaining the solid phase apparatus under conditions which allow fluid to transport contacted first analyte binding particles and contacted second analyte binding particles by capillary action through the solid phase apparatus to and through each sample capture zone, thereby allowing contacted first analyte binding particles to bind to the first sample capture reagent in the first sample capture zone, and allowing contacted second analyte binding particles to bind to the second sample capture reagent in the second sample capture zone; and allowing the fluid in the sample to transport contacted first analyte binding particles and contacted second analyte binding particles by capillary action through the solid phase apparatus to and through the control capture zone, thereby allowing contacted first analyte binding particles and contacted second analyte binding particles to bind to the control capture reagent;

f) determining the amount of contacted first analyte binding particles in the first sample capture zone, the amount of contacted second analyte binding particles in the second capture zone, and the amount of contacted first analyte binding particles and contacted second analyte binding particles in the control capture zone;

g) determining a first corrected analyte binding particle amount as a ratio of the amount of contacted first analyte binding particles in the first sample capture zone to the sum of the amount of contacted first analyte binding particles in the first sample capture zone, the amount of contacted second analyte binding particles in the second sample capture zone, and amount of contacted first analyte binding particles and contacted second analyte binding particles in the control capture zone; and a second corrected analyte binding particle amount as a ratio of the amount of contacted second analyte binding particles in the second sample capture zone to the sum of the amount of contacted first analyte binding particles in the first sample capture zone, the amount of contacted second analyte binding particles in the second sample capture zone, and the amount of contacted first analyte binding particles and second analyte binding particles in the control capture zone, wherein the amount of the first analyte of interest in the fluid sample is directly related to the first corrected analyte binding particle amount, and the amount of the second analyte of interest in the fluid sample is directly related to the second corrected analyte binding particle amount.

2. The method of claim 1, further comprising quantitatively measuring the amount of one or more additional analytes of interest, wherein the solid phase apparatus comprises an additional sample capture zone for each additional analyte of interest, each additional sample capture zone having a sample capture reagent adsorbed thereon; wherein a sample collection apparatus further contains a population of additional analyte binding particles for each additional analyte of interest; wherein the solid phase apparatus is maintained under conditions which allow fluid to transport contacted additional analyte binding particles by capillary action through the solid phase apparatus to and through each sample capture zone, thereby allowing contacted additional analyte binding particles to bind to the additional sample capture reagent in each additional sample capture zone; wherein a corrected analyte binding particle amount is determined for each analyte of interest as a ratio of the amount of contacted additional analyte binding particles in each corresponding additional sample capture zone to the amount of all analyte binding particles in all of the sample capture zones and the control capture zone, and wherein the amount of each analyte of interest in the fluid sample is directly related to a corresponding corrected analyte binding particle amount.

3. The method of claim 1, wherein a detected background amount is subtracted from the determined amount of particles in each zone prior to determining the ratio.

4. A method of measuring an amount of at least two analytes of interest in a test sample, comprising:

a) providing a solid phase apparatus comprising an application point, at least two sample capture zones, and a control capture zone; the first sample capture zone having a first sample capture reagent adsorbed thereon, the second sample capture zone having a second sample capture reagent adsorbed thereon, and the control capture zone having a control capture reagent adsorbed thereon; wherein the application point, the first sample zone, second capture zone, and control capture zone are sequentially located on the solid phase apparatus;

b) providing a sample collection apparatus containing a population of first analyte binding particles and a population of second analyte binding particles, wherein the first analyte binding particles are coated with a first analyte binding agent and the second analyte binding particles are coated with a second analyte binding agent;

c) introducing a fluid sample and a buffer into the sample collection apparatus, thereby producing a buffered, mixed fluid sample comprising contacted first analyte binding particles and contacted second analyte binding particles;

d) applying the buffered, mixed fluid sample to the application point of the solid phase apparatus;

e) maintaining the solid phase apparatus under conditions which allow fluid to transport contacted first analyte binding particles and contacted second analyte binding particles by capillary action through the solid phase apparatus to and through each sample capture zone, thereby allowing contacted first analyte binding particles to bind to the first sample capture reagent in the first sample capture zone, and allowing contacted second analyte binding particles to bind to the second sample capture reagent in the second sample capture zone; and allowing the fluid in the sample to transport contacted first analyte binding particles and contacted second analyte binding particles by capillary action through the solid phase apparatus to and through the control capture zone, thereby allowing contacted first analyte binding particles and contacted second analyte binding particles to bind to the control capture reagent;

f) determining the amount of contacted first analyte binding particles in the first sample capture zone, the amount of contacted second analyte binding particles in the second capture zone, and the amount of contacted first analyte binding particles and contacted second analyte binding particles in the control capture zone;

g) determining a first corrected analyte binding particle amount as a ratio of the amount of contacted first analyte binding particles in the first sample capture zone to the sum of the amount of contacted first analyte binding particles in the first sample capture zone, the amount of contacted second analyte binding particles in the second sample capture zone, and amount of contacted first analyte binding particles and contacted second analyte binding particles in the control capture zone; and a second corrected analyte binding particle amount as a ratio of the amount of contacted second analyte binding particles in the second sample capture zone to the sum of the amount of contacted first analyte binding particles in the first sample capture zone, the amount of contacted second analyte binding particles in the second sample capture zone, and the amount of contacted first analyte binding particles and contacted second analyte binding particles in the control capture zone, wherein the amount of the first analyte of interest in the fluid sample is directly related to the first corrected analyte binding particle amount, and the amount of the second analyte of interest in the fluid sample is directly related to the second corrected analyte binding particle amount.

5. The method of claim 4, further comprising quantitatively measuring the amount of one or more additional analytes of interest, wherein the solid phase apparatus comprises an additional sample capture zone for each additional analyte of interest, each additional sample capture zone having a sample capture reagent adsorbed thereon; wherein a sample collection apparatus further contains a population of additional analyte binding particles for each additional analyte of interest; wherein the solid phase apparatus is maintained under conditions which allow fluid to transport contacted additional analyte binding particles by capillary action through the solid phase apparatus to and through each sample capture zone, thereby allowing contacted additional analyte binding particles to bind to the additional sample capture reagent in each additional sample capture zone; wherein a corrected analyte binding particle amount is determined for each analyte of interest as a ratio of the amount of contacted additional analyte binding particles in each corresponding additional sample capture zone to the amount of all analyte binding particles in all of the sample capture zones and the control capture zone, and wherein the amount of each analyte of interest in the fluid sample is directly related to a corresponding corrected analyte binding particle amount.

6. The method of claim 4, wherein a detected background amount is subtracted from the determined amount of particles in each zone prior to determining the ratio.

* * * * *